(12) United States Patent
Kim et al.

(10) Patent No.: US 12,296,054 B2
(45) Date of Patent: May 13, 2025

(54) METHOD OF PREPARING POLYMERIC MICROPARTICLES, POLYMERIC MICROPARTICLES, MEDICAL COMPOSITION, COSMETIC COMPOSITION, MEDICAL ARTICLES AND COSMETIC ARTICLES USING THE SAME

(71) Applicant: LG CHEM, LTD., Seoul (KR)

(72) Inventors: Yunseop Kim, Daejeon (KR); Jung Youn Shin, Daejeon (KR); Chanjoong Kim, Daejeon (KR); Jee Seon Kim, Daejeon (KR); Kyung Oh Kim, Daejeon (KR); Je Young Ryu, Daejeon (KR)

(73) Assignee: LG CHEM, LTD., Seoul (KR)

( * ) Notice: Subject to any disclaimer, the term of this patent is extended or adjusted under 35 U.S.C. 154(b) by 516 days.

(21) Appl. No.: 17/640,923

(22) PCT Filed: Jun. 1, 2021

(86) PCT No.: PCT/KR2021/006828
§ 371 (c)(1),
(2) Date: Mar. 7, 2022

(87) PCT Pub. No.: WO2021/246764
PCT Pub. Date: Dec. 9, 2021

(65) Prior Publication Data
US 2022/0331260 A1    Oct. 20, 2022

(30) Foreign Application Priority Data

Jun. 1, 2020 (KR) .................. 10-2020-0066053
May 31, 2021 (KR) .................. 10-2021-0070287

(51) Int. Cl.
*A61K 9/50*    (2006.01)
*A61K 8/11*    (2006.01)
(Continued)

(52) U.S. Cl.
CPC .............. *A61K 9/5057* (2013.01); *A61K 8/11* (2013.01); *A61K 8/19* (2013.01); *A61K 8/65* (2013.01);
(Continued)

(58) Field of Classification Search
None
See application file for complete search history.

(56) References Cited

U.S. PATENT DOCUMENTS 6,375,988 B1    4/2002    Suzuki et al.
2003/0109497 A1    6/2003    Wehner et al.
(Continued)

FOREIGN PATENT DOCUMENTS

CN    103816573 A    5/2014
CN    109071832 A    12/2018
(Continued)

OTHER PUBLICATIONS

Wang et al ("Novel crosslinked alginate/hyaluronic acid hydrogels for nerve tissue engineering", vol. 7(3) (2013), p. 269-284) (Year: 2013).*
(Continued)

*Primary Examiner* — Sin J Lee
(74) *Attorney, Agent, or Firm* — ROTHWELL, FIGG, ERNST & MANBECK, P.C.

(57) ABSTRACT

According to the present disclosure, a method of preparing polymeric microparticles comprising further crosslinking with an organic crosslinking agent after crosslinking with metal ions, polymeric microparticles, medical compositions, cosmetic compositions, medical articles and cosmetic articles comprising the same can be provided.

18 Claims, 2 Drawing Sheets

(51) Int. Cl.

| | | |
|---|---|---|
| *A61K 8/19* | (2006.01) | |
| *A61K 8/65* | (2006.01) | |
| *A61K 8/73* | (2006.01) | |
| *A61Q 19/00* | (2006.01) | |
| *C08J 3/12* | (2006.01) | |
| *C08J 3/24* | (2006.01) | |
| *C08L 5/08* | (2006.01) | |

(52) U.S. Cl.
 CPC ............ *A61K 8/735* (2013.01); *A61K 9/5036* (2013.01); *A61K 9/5089* (2013.01); *A61Q 19/00* (2013.01); *C08J 3/12* (2013.01); *C08J 3/126* (2013.01); *C08J 3/245* (2013.01); *C08L 5/08* (2013.01); *A61K 2800/10* (2013.01); *A61K 2800/412* (2013.01); *A61K 2800/651* (2013.01); *A61K 2800/652* (2013.01); *C08J 2305/08* (2013.01); *C08J 2405/08* (2013.01)

(56) References Cited

U.S. PATENT DOCUMENTS

| | | |
|---|---|---|
| 2004/0191299 A1 | 9/2004 | Hinotani et al. |
| 2005/0161844 A1 | 7/2005 | Dunfield et al. |
| 2011/0200658 A1 | 8/2011 | Mulqueen et al. |
| 2011/0263018 A1 | 10/2011 | Park et al. |
| 2012/0164098 A1 | 6/2012 | Schroeder et al. |
| 2015/0183891 A1 | 7/2015 | Giammona et al. |
| 2016/0083690 A1 | 3/2016 | Birch et al. |
| 2016/0088838 A1 | 3/2016 | Mulqueen et al. |
| 2017/0304458 A1 | 10/2017 | Van Spreuwel-Goossens |
| 2018/0215840 A1 | 8/2018 | Choi et al. |
| 2018/0360031 A1 | 12/2018 | Mulqueen et al. |
| 2019/0176125 A1 | 6/2019 | Yoon et al. |
| 2019/0315887 A1 | 10/2019 | Choi et al. |
| 2020/0276230 A1 | 9/2020 | Stock et al. |
| 2021/0017348 A1 | 1/2021 | Lee et al. |
| 2021/0244668 A1 | 8/2021 | Loscalzo et al. |
| 2022/0081684 A1 | 3/2022 | Kim et al. |
| 2022/0298310 A1 | 9/2022 | Kim et al. |
| 2022/0331260 A1 | 10/2022 | Kim et al. |
| 2023/0348675 A1 | 11/2023 | Garigapati et al. |

FOREIGN PATENT DOCUMENTS

| | | |
|---|---|---|
| EP | 0913149 A1 | 5/1999 |
| EP | 3995531 A1 | 5/2022 |
| JP | H10-067687 A | 3/1998 |
| JP | H11-130697 A | 5/1999 |
| JP | 2005-211898 A | 8/2005 |
| JP | 2012-510535 A | 5/2012 |
| JP | 2014519843 A | 8/2014 |
| JP | 2015-178099 A | 10/2015 |
| JP | 2019-512522 A | 5/2019 |
| JP | 2019-523285 A | 8/2019 |
| KR | 10-1999-0037094 A | 5/1999 |
| KR | 10-2004-0018927 A | 3/2004 |
| KR | 10-2004-0021615 A | 3/2004 |
| KR | 10-2007-0004159 A | 1/2007 |
| KR | 10-2008-0073419 A | 8/2008 |
| KR | 10-0871652 B1 | 12/2008 |
| KR | 10-0910930 B1 | 8/2009 |
| KR | 10-2011-0118859 A | 11/2011 |
| KR | 10-1304949 B1 | 9/2013 |
| KR | 10-2016-0041616 A | 4/2016 |
| KR | 10-1732609 B1 | 5/2017 |
| KR | 10-1761544 B1 | 7/2017 |
| KR | 10-2017-0090965 A | 8/2017 |
| KR | 10-2018-0003443 A | 1/2018 |
| KR | 10-1929293 B1 | 12/2018 |
| KR | 10-2019-0062760 A | 6/2019 |
| KR | 10-2020-0048476 A | 5/2020 |
| KR | 10-2201482 B1 | 1/2021 |
| KR | 10-2021-0011340 A | 2/2021 |
| WO | 2003-002075 A1 | 1/2003 |
| WO | 2012177257 A1 | 12/2012 |
| WO | 2016-063935 A1 | 4/2016 |
| WO | 2019-097250 A1 | 5/2019 |
| WO | 2019-194543 A | 10/2019 |
| WO | 2021060934 A1 | 4/2021 |
| WO | 2023054901 A1 | 4/2023 |

OTHER PUBLICATIONS

International Search Report issued for International Application No. PCT/KR2021/006828 on Sep. 13, 2021, 4 pages.

Jui-Yang Lai, "Biofunctionalization of gelatin microcarrier with oxidized hyaluronic acid for corneal keratocyte cultivation", Colloids and Surfaces B: Biointerfaces, (2014) vol. 122, pp. 277-286.

Kabir-ud-Din et al.. "Micellization and Clouding Phenomenon of Phenothiazine Drug Promethazine Hydrochloride: Effect of NaCl and Urea Addition", Journal of Dispersion Science and Technology, (2010) vol. 31, pp. 1182-1187.

Kim, et al., "Preparation of Hyaluronic Acid Microspheres with Enhanced Physical Stability by Double Cross-link or Alginate", Yakhak Hoeji, (2011) vol. 55, No. 1, pp. 69-74.

Extended European Search Report dated Oct. 17, 2022, of the corresponding European Patent Application No. 21818529.6, 7 pages.

Extended European Search Report dated May 17, 2024 for the corresponding European Patent Application No. 22876677.0, 8 pages.

\* cited by examiner

METHOD OF PREPARING POLYMERIC MICROPARTICLES, POLYMERIC MICROPARTICLES, MEDICAL COMPOSITION, COSMETIC COMPOSITION, MEDICAL ARTICLES AND COSMETIC ARTICLES USING THE SAME

TECHNICAL FIELD

Cross-Reference to Related Application(s)

This application is a 35 U.S.C. 371 National Phase Entry Application from PCT/KR2021/006828, filed on Jun. 1, 2021, which claims the benefit of Korean Patent Application No. 10-2020-0066053 filed on Jun. 1, 2020 and Korean Patent Application No. 10-2021-0070287 filed on May 31, 2021 in the Korean Intellectual Property Office, all of the disclosures of which are incorporated herein by reference in their entirety.

The present disclosure relates to a method of preparing polymeric microparticles that can realize excellent mechanical strength and stability, polymeric microparticles, medical compositions, cosmetic compositions, medical articles and cosmetic articles comprising the same.

BACKGROUND OF THE INVENTION

Along with the expansion of the fields of biopharmaceuticals and regenerative medicine, the need for the large-scale culture techniques capable of efficiently producing cells, tissues, microorganisms, and the like is growing.

Adherent cells are cultured using microcarriers within a 3D bioreactor. A cell, a culture medium, and a microcarrier are put in a bioreactor, and the cells are brought into contact with the microcarrier while stirring the culture medium, so that the cells are attached to the surface of the microcarrier and cultured. Since the microcarrier used at this time provides a high surface area/volume to which cells can attach and proliferate, it is suitable for large-scale culture of cells. However, when the adherent cells are expanded and cultured using a microcarrier, a process of recovering cells through the process of cell detachment is essentially involved after completion of cultivation. The cell detachment process induces cell detachment by using a proteolytic enzyme or changing the temperature. When such a detachment process is added, there is a problem that the manufacturing cost is increased, the economic efficiency is lowered, and cell damage may be induced.

The development of new materials and processes to solve these problems is steadily progressing. In particular, in the case of a cell therapeutic agent for injecting in vivo cells, attempts were made to ensure the biocompatibility of the microcarrier for culturing the cells and to omit the isolation and purification process. In this case, particles that implement the strength capable of withstanding the stress applied by fluid around the carrier during the culture process and after injection into the living body are necessary.

In addition, in the case of transdermal drug delivery technology in which a microcarrier that collects drugs or bioactive substances is mounted on a microneedle and delivered, the microcarrier must use a polymer suitable for applying to the living body, and it must have sufficient strength so that particles do not deform in the process of passing through the stratum corneum layer of the skin. Microcarriers that stably permeate the skin can deliver the loaded drug locally or systemically, allowing them to act on the required lesions.

Hyaluronic acid mainly used as a biocompatible substance is composed of N-acetyl-D-glucosamine and D-glucuronic acid, and is a biopolymer in which the repeating units are linearly linked. Hyaluronic acid is abundantly present in the vitreous humor of the eyeball, the synovial fluid of the joints, and cockscomb, and the like. Hyaluronic acid is commonly used as bioinjectable materials due to its excellent biocompatibility and viscoelasticity, but is in itself easily decomposed in vivo or under conditions such as acid or alkali, and thus, its use is limited. Further, when applied to microcarriers, there was a problem that hyaluronic acid exhibits a negative charge in the biological pH range and thus significantly reduces cell adhesion.

Further, gelatin is a polymer obtained by hydrolyzing collagen, which is a bio-connective tissue, and is often used as a scaffold for cell culture. Gelatin can collect or culture the cells, but it is weak in the strength and is sensitive to temperature, so that researches were conducted to improve its strength by introducing a functional group by a chemical method.

Therefore, it is necessary to develop microcarriers or polymeric microparticles that are compatible with the living body and have excellent physical properties, such as physical strength, and stability against heat and enzymes, and excellent stability.

BRIEF SUMMARY OF THE INVENTION

It is one object of the present disclosure to provide a method of preparing polymeric microparticles that can realize excellent mechanical strength and stability.

It is another object of the present disclosure to provide polymeric microparticles prepared by the above-mentioned preparation method.

It is another object of the present disclosure to provide a medical composition comprising the above-mentioned polymeric microparticles.

It is yet another object of the present disclosure to provide a cosmetic composition comprising the above-mentioned polymeric microparticles.

It is yet another object of the present disclosure to provide a medical article comprising the above-mentioned medical composition.

It is a further object of the present disclosure to provide a cosmetic article comprising the above-mentioned cosmetic composition.

In order to achieve the above object, according to one aspect, there is provided a method of preparing polymeric microparticles comprising the steps of: reacting a mixture containing a biocompatible polymer and a metal ion to form crosslinked polymer particles; and further crosslinking the crosslinked polymer particles in a polar solvent phase including an organic crosslinking agent containing at least one reactive functional group.

According to another aspect, there is provided polymeric microparticles having a core-shell structure, which comprises: a core including a first biocompatible polymer, a metal ion, and an organic crosslinking agent containing at least one reactive functional group; and a shell surrounding all or part of the core and including a second biocompatible polymer, a metal ion, and an organic crosslinking agent containing at least one reactive functional group.

According to another aspect, there is provided a medical composition comprising the polymeric microparticles and a pharmaceutically effective substance contained in the polymeric microparticles.

According to yet another aspect, there is provided a cosmetic composition comprising the polymeric microparticles and a cosmetically effective substance contained in the polymeric microparticles.

According to yet another aspect, there is provided a medical article comprising the medical composition.

According to a further aspect, there is provided a cosmetic article comprising the cosmetic composition.

DETAILED DESCRIPTION OF THE INVENTION

Hereinbelow, a method of preparing polymeric microparticles, polymeric microparticles, medical compositions, cosmetic compositions, medical articles and cosmetic articles comprising the same according to specific embodiments of the present disclosure will be described in more detail.

Unless otherwise specified throughout this specification, the technical terms used herein are only for reference to specific embodiments and is not intended to limit the present disclosure.

The singular forms "a", "an", and "the" used herein include plural references unless the context clearly dictates otherwise.

The term "including" or "comprising" used herein specifies a specific feature, region, integer, step, action, element and/or component, but does not exclude the presence or addition of a different specific feature, region, integer, step, action, element, component and/or group.

The terms including ordinal numbers such as "a first", "a second", etc. are used only for the purpose of distinguishing one component from another component, and are not limited by the ordinal numbers. For instance, a first component may be referred to as a second component, or similarly, the second component may be referred to as the first component, without departing from the scope of the present disclosure.

In the present disclosure, the (co)polymer means including both a polymer and a copolymer, the polymer means a homopolymer consisting of a single repeating unit, and the copolymer means a composite polymer containing two or more repeating units.

Although the present disclosure may have various forms and various modifications may be made thereto, specific examples will be exemplified and explained in detail below. However, it is not intended to limit the present disclosure to specific disclosure, and it should be understood that the present disclosure includes all the modifications, equivalents or replacements thereof without departing from the spirit and technical scope of the invention.

As used herein, the microparticle means that the cross section of the particle is circular or elliptical, and the ratio (sphericity degree) of minor axis/major axis of the particle is in the range of 0.7 to 1.0. The length of the minor axis and the major axis of the particles can be derived by taking an optical picture of the particles and calculating the average value of 30~100 arbitrary particles in an optical picture.

In the present disclosure, the diameter Dn means the diameter at n volume % point of cumulative distribution of the particle numbers depending on the diameter. That is, D50 is the diameter at 50% point of cumulative distribution of the particle numbers when the diameters of the particles are accumulated in ascending order, D90 is the diameter at 90% point of cumulative distribution of particle numbers depending on the diameter, and D10 is the diameter at 10% point of cumulative distribution of the particle numbers depending on the diameter.

The Dn can be measured by using a laser diffraction method. Specifically, the powder to be measured is dispersed in a dispersion medium and then introduced into a commercially available laser diffraction particle size measurement instrument (Horiba LA-960), a diffraction pattern difference according to the particle size is measured when the particles pass through a laser beam, and the particle size distribution is calculated. The particle diameter at points of 10%, 50% and 90% of the particle number cumulative distribution depending on the diameter can be calculated in a measuring device to thereby measure D10, D50, and D90. More specifically, in the present disclosure, the diameter may mean D50.

As used herein, the emulsion means a mixed phase in which one or more liquids that are immiscible with an oil phase or an aqueous phase are dispersed in another liquid (dispersion medium) in a particulate form (dispersoid). The emulsion can usually be divided into macroemulsions, microemulsions and nanoemulsions, depending on the particle size of the dispersed phase.

Now, the present disclosure will be described in more detail.

1. Method of Preparing Polymeric Microparticles

According to one embodiment of the present disclosure, there can be provided a method of preparing polymeric microparticles comprising the steps of: reacting a mixture containing a biocompatible polymer and a metal ion to form crosslinked polymer particles; and further crosslinking the crosslinked polymer particles in a polar solvent phase including an organic crosslinking agent containing at least one reactive functional group.

In conventional polymeric microparticles, as crosslinking is performed after forming a W/O emulsion using oil, an oil washing process is essentially needed, and thus, there was a technical problem that not only the process efficiency is deteriorated, but also it is difficult to remove a residual oil.

In view of the above, the present inventors have found through experiments that as a crosslinking reaction is performed by a metal ion and then a further crosslinking reaction is performed using an organic crosslinking agent containing at least one reactive functional group as in the method of preparing the polymeric microparticles of the one embodiment, the process efficiency is maximized and, at the same time, the mechanical strength and stability of microparticles are remarkably improved, thereby completing the present disclosure.

Specifically, the biocompatible polymer means a polymer that can be injected directly into a human body in order to deliver effective substances applied to the human body. Specifically, the biocompatible polymer may be at least one polymer selected from the group consisting of hyaluronic acid (HA), carboxymethyl cellulose (CMC), alginic acid, pectin, carrageenan, chondroitin (sulphate), dextran (sulfate), chitosan, polylysine, collagen, gelatin, carboxymethyl chitin, fibrin, agarose, pullulan, polylactide, polyglycolide (PGA), polylactide-glycolide copolymer (PLGA), polyanhydride, polyorthoester, polyetherester, polycaprolactone, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefins, polyethylene oxide, polyvinylpyrrolidone (PVP), polyethylene glycol (PEG), polymethacrylate, hydroxypropylmethylcellulose (HPMC), ethyl cellulose (EC), hydroxypropyl cellulose (HPC), cyclodextrin, copolymers of monomers forming these polymers, and cellulose.

More specifically, the biocompatible polymer may be a mixture of hyaluronic acid (HA) and gelatin.

Polymeric microparticles prepared using only hyaluronic acid are easily decomposed in vivo or under conditions such as acid and alkali, and therefore, their use is limited, cell adhesion is remarkably reduced, and polymeric microparticles prepared by using only gelatin are significantly reduced in the mechanical properties.

Therefore, a mixture of hyaluronic acid (HA) and gelatin can be used as a biocompatible polymer, thereby realizing excellent cell adhesion and mechanical properties at the same time.

As used herein, the hyaluronic acid may mean including both hyaluronic acid itself and a hyaluronic acid salt. Therefore, the hyaluronic acid aqueous solution may be a concept that includes both an aqueous solution of hyaluronic acid, an aqueous solution of a hyaluronic acid salt, and a mixed aqueous solution of hyaluronic acid and a hyaluronic acid salt. The salt of hyaluronic acid may be inorganic salts such as sodium hyaluronate, potassium hyaluronate, calcium hyaluronate, magnesium hyaluronate, zinc hyaluronate, cobalt hyaluronate, organic salts such as hyaluronic acid tetrabutylammonium, and mixtures thereof.

In one embodiment of the present disclosure, the molecular weight of hyaluronic acid is not particularly limited, but is preferably 10,000 g/mol or more and 5,000,000 g/mol or less in order to realize various physical properties and biocompatibility.

As used herein, the gelatin may mean a protein obtained by treating collagen derived from an animal with acid or alkali and subsequently extracting it.

In one embodiment of the present disclosure, the molecular weight of gelatin is not particularly limited, but is preferably 10,000 g/mol or more and 5,000,000 g/mol or less in order to realize various physical properties and biocompatibility.

In one embodiment of the present disclosure, the mixture of hyaluronic acid (HA) and gelatin may contain gelatin in an amount of 50 parts by weight or more and 500 parts by weight or less, 100 parts by weight or more and 500 parts by weight or less, or 100 parts by weight or more and 300 parts by weight or less with respect to 100 parts by weight of hyaluronic acid (HA).

When gelatin is contained an amount of less than 50 parts by weight with respect to 100 parts by weight of hyaluronic acid (HA), cell adhesion of the prepared polymeric microparticles may be deteriorated. When gelatin is contained in an amount of more than 500 parts by weight with respect to 100 parts by weight of hyaluronic acid (HA), the mechanical properties of the prepared polymeric microparticles may be reduced. That is, as the mixture of hyaluronic acid (HA) and gelatin contains gelatin in an amount of 50 parts by weight or more and 500 parts by weight or less with respect to 100 parts by weight of hyaluronic acid (HA), it is possible to prepare polymeric microparticles capable of realizing excellent cell adhesion and mechanical properties at the same time.

In one embodiment of the present disclosure, the metal ion may include one selected from the group consisting of iron ion ($Fe^{3+}$), aluminum ion ($Al^{3+}$), copper ion ($Cu^{2+}$), iron ion ($Fe^{2+}$), magnesium ion ($Mg^{2+}$), barium ion ($Ba^{2+}$), calcium ion ($Ca^{2+}$), and the like. More specifically, the metal ion may be an iron ion, an aluminum ion, or a mixture thereof.

In one embodiment of the present disclosure, the step of reacting a mixture containing a biocompatible polymer and a metal ion to form crosslinked polymer particles may include forming an aqueous solution in which the biocompatible polymer is dissolved; adding a compound containing the metal ion to a polar solvent to form a solution containing the metal ion; and mixing an aqueous solution droplet in which the biocompatible polymer is dissolved and a solution containing the metal ion to form a mixed solution.

Specifically, in the step of forming the aqueous solution in which the biocompatible polymer is dissolved, the aqueous solution in which the biocompatible polymer is dissolved may contain the biocompatible polymer in an amount of 0.01% by weight or more and 10% by weight or less, 0.01% by weight or more and 5% by weight or less, and 1% by weight or more and 5% by weight or less. 1% by weight or more and 3% by weight or less, 2% by weight or more and 3% by weight or less, 2% by weight or more and 2.5% by weight or less with respect to the entire weight of the aqueous solution in which the biocompatible polymer is dissolved.

As in one embodiment of the present disclosure, as a crosslinking reaction proceed by a metal ion and then a further cros slinking reaction proceeds by an organic cros slinking agent containing at least one reactive functional group, microparticles having excellent mechanical strength and stability can be prepared even by using the biocompatible polymer in a small content of 0.01% by weight or more and 10% by weight or less, as compared with the case where the crosslinking reaction proceeds after forming the W/O emulsion as in the conventional case.

The step of adding the compound containing the metal ion to the polar solvent to form the solution containing the metal ion is not particularly limited, but for example, it can be formed by dispersing the compound containing the metal ion in a polar solvent such as ethanol.

Further, in the step of mixing an aqueous solution droplet in which the biocompatible polymer is dissolved and a solution containing the metal ion to form a mixed solution, the size of the particles can be appropriately controlled by using an encapsulator (BUCHI, B-390) equipment.

By including the step of mixing the aqueous solution droplets in which the biocompatible polymer is dissolved and the solution containing the metal ion to form a mixed solution, the metal ion is chelated to the biocompatible polymer and the biocompatible polymer can form a crosslinked structure through the metal ion.

As one embodiment of the present disclosure includes the step of reacting a mixture containing a biocompatible polymer and a metal ion to form crosslinked polymer particles, it is possible to prepare microparticles in a polar solvent phase without using oil, thereby omitting the oil washing process and realizing the effect of improving process efficiency, as compared with the case where the crosslinking reaction is performed using only an organic crosslinking agent containing at least one reactive functional group.

That is, as the metal ion is chelated to the biocompatible polymer and the biocompatible polymer forms a crosslinked structure through the metal ion, it is possible to prepare microparticles in a polar solvent phase without using oil, thereby omitting the oil washing process and realizing the effect of improving process efficiency, as compared with the case where the crosslinking reaction is performed using only an organic crosslinking agent containing at least one reactive functional group.

In addition, the compound containing the metal ion may be contained in an amount of 200 parts by weight or more and 1000 parts by weight or less, 300 parts by weight or more and 1000 parts by weight or less, or 500 parts by weight or more and 1000 parts by weight or less with respect to 100 parts by weight of the biocompatible polymer.

In the method of preparing polymeric microparticles according to one embodiment of the present disclosure, as a further crosslinking reaction proceeds after a crosslinking reaction with a metal ion as described above, polymeric microparticles that realize sufficient mechanical strength and sphericity degree can be prepared even if a mixture containing the metal ion is added in a small amount of 200 parts by weight or more to 1000 parts by weight or less with respect to 100 parts by weight of the biocompatible polymer.

When the compound containing the metal ion is added in a content of more than 1000 parts by weight with respect to 100 parts by weight of the biocompatible polymer, a technical problem may occur in which a residual amount of metal ions remains in the crosslinked particles.

The organic crosslinking agent containing at least one reactive functional group may include a crosslinking agent having 1 to 30 carbon atoms and containing at least one reactive functional group.

As described above, as a crosslinking reaction proceeds by metal ions and then a further crosslinking reaction proceeds using a crosslinking agent having 1 to 30 carbon atoms and containing at least one reactive functional group, the process efficiency is maximized and, at the same time, the mechanical strength and stability of the microparticles can be significantly improved.

The type of the reactive functional group is not particularly limited, and examples thereof include a hydroxyl group, an epoxy group, a carboxy group, an amino group, a (meth)acrylate group, a nitrile group, a thiol group, an aldehyde group, or a vinyl group.

Specifically, the organic crosslinking agent containing at least one reactive functional group may include one or more, or two or more formyl groups or epoxy groups. The formyl group or the epoxy group may be a crosslinkable functional group that reacts with the above-mentioned biocompatible polymer to form crosslinked particles.

In the embodiment of the present disclosure, examples of the organic crosslinking agent containing at least one reactive functional group are not particularly limited. Specifically, the crosslinking agent may include one selected from the group consisting of glutaraldehyde, 1,4-butandiol diglycidyl ether (BDDE), ethylene glycol diglycidyl ether (EGDGE), 1,6-hexanediol diglycidyl ether, propylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylpropane polyglycidyl ether, 1,2-(bis(2,3-epoxypropoxy)ethylene, pentaerythritol polyglycidyl ether, sorbitol polyglycidyl ether, divinylsulfone, and epichlorohydrin.

More specifically, the organic cros slinking agent containing at least one reactive functional group may be glutaraldehyde or 1,4-butandiol diglycidyl ether (BDDE).

On the other hand, in the step of further crosslinking the crosslinked polymer particles in a polar solvent phase including an organic crosslinking agent containing at least one reactive functional group, the organic crosslinking agent containing at least one reactive functional group can be contained in an amount of 150 parts by weight or more and 1000 parts by weight or less, 200 parts by weight or more and 1000 parts by weight or less, 300 parts by weight or more and 800 parts by weight or less, 400 parts by weight or more and 500 parts by weight or less with respect to 100 parts by weight of the biocompatible polymer.

In the method of preparing polymeric microparticles according to one embodiment of the present disclosure, as the further crosslinking reaction proceeds after the crosslinking reaction with metal ions as described above, polymeric microparticles that realize sufficient mechanical strength and sphericity degree can be prepared even if an organic crosslinking agent containing at least one reactive functional group is added in a small amount of 150 parts by weight or more and 1000 parts by weight or less with respect to 100 parts by weight of the biocompatible polymer.

When the organic crosslinking agent containing at least one reactive functional group is added in a content of more than 1000 parts by weight with respect to 100 parts by weight of the biocompatible polymer, a technical problem may occur in which a residual amount of the unreacted crosslinking agent remains in the crosslinked particles.

On the other hand, in the step of further crosslinking the crosslinked polymer particles in a polar solvent phase including an organic crosslinking agent containing at least one reactive functional group, types of the polar solvent are not particularly limited, and examples thereof may be one selected from the group consisting of ethanol, N,N-dimethylformamide, N,N-dimethylacetamide, N-methyl-2-pyrrolidone, N-methylcaprolactam, 2-pyrrolidone, N-ethylpyrrolidone, N-vinylpyrrolidone, dimethyl sulfoxide, tetramethylurea, pyridine, dimethyl sulfone, hexamethyl sulfoxide, gamma-butyrolactone, 3-methoxy-N,N-dimethylpropanamide, 3-ethoxy-N,N-dimethylpropanamide, 3-butoxy-N,N-dimethylpropanamide, 1,3-dimethyl-imidazolidinone, ethyl amyl ketone, methyl nonyl ketone, methyl ethyl ketone, methyl isoamyl ketone, methyl isopropyl ketone, cyclohexanone, ethylene carbonate, propylene carbonate, diglyme, 4-hydroxy-4-methyl-2-pentanone, ethylene glycol monomethyl ether, ethylene glycol monomethyl ether acetate, ethylene glycol monoethyl ether, ethylene glycol monoethyl ether acetate, ethylene glycol monopropyl ether, ethylene glycol monopropyl ether acetate, ethylene glycol monoisopropyl ether, ethylene glycol monoisopropyl ether acetate, ethylene glycol monobutyl ether, and ethylene glycol monobutyl ether acetate.

Further, in the step of further crosslinking the crosslinked polymer particles in a polar solvent phase including an organic crosslinking agent containing at least one reactive functional group, the polar solvent phase including the organic crosslinking agent containing at least one reactive functional group may be an alkaline mixed solvent.

That is, the further crosslinking reaction of the present disclosure can be performed in an alkaline mixed solvent phase in which an alkaline aqueous solution is mixed with a polar solvent. Examples of the alkaline aqueous solution is not so limited, but may be, for example, a sodium hydroxide aqueous solution.

As the polar solvent including the organic crosslinking agent containing at least one reactive functional group is an alkaline mixed solvent, it is possible to create an environment favorable for the nucleophilic substitution reaction (SN reaction) to increase the efficiency of the cros slinking reaction.

2. Polymeric Microparticles

According to one embodiment of the present disclosure, there can be provided polymeric microparticles having a core-shell structure, which comprises: a core including a first biocompatible polymer, a metal ion, and an organic crosslinking agent containing at least one reactive functional group; and a shell surrounding all or part of the core and including a second biocompatible polymer, a metal ion, and an organic crosslinking agent containing at least one reactive functional group.

The present inventors proceeded with research on polymeric microparticles, and confirmed through experiments that as a further crosslinking reaction proceeds after a crosslinking reaction with metal ion as described above, the process efficiency is maximized, and at the same time, the mechanical strength and cell adhesion of the microparticles are remarkably improved, thereby completing the present disclosure.

In one embodiment of the present disclosure, the core may include a polymer matrix in which the first biocompatible polymer is crosslinked through a metal ion and an organic crosslinking agent containing at least one reactive functional group, and the shell may include a polymer matrix in which the second biocompatible polymer is crosslinked through a metal ion and an organic crosslinking agent containing at least one reactive functional group.

Specifically, the polymer matrix may include a first crosslinking region in which the biocompatible polymer is crosslinked through a metal ion; and a second crosslinking region in which the biocompatible polymer is crosslinked through an organic crosslinking agent containing at least one reactive functional group.

The first crosslinking region means a crosslinking region formed by a crosslinking reaction between the biocompatible polymer and the metal ion, and the second crosslinking region may mean a crosslinking region formed by a crosslinking reaction with an organic crosslinking agent containing at least one reactive functional group instead of a crosslinking reaction between the biocompatible polymer and the metal ion, and a cros slinking region formed through a further crosslinking reaction of the first crosslinking region and an organic crosslinking agent containing at least one reactive functional group. That is, the polymeric microparticles of the embodiment may be prepared through a crosslinking reaction using a metal ion and an organic crosslinking agent containing at least one reactive functional group.

Specifically, the biocompatible polymer is a polymer that can be injected directly into a human body in order to deliver effective substances applied to the human body. Specifically, the biocompatible polymer may be at least one polymer selected from the group consisting of hyaluronic acid (HA), carboxymethyl cellulose (CMC), alginic acid, pectin, carrageenan, chondroitin (sulphate), dextran (sulfate), chitosan, polylysine, collagen, gelatin, carboxymethyl chitin, fibrin, agarose, pullulan, polylactide, polyglycolide (PGA), polylactide-glycolide copolymer (PLGA), polyanhydride, polyorthoester, polyetherester, polycaprolactone, polyesteramide, poly(butyric acid), poly(valeric acid), polyurethane, polyacrylate, ethylene-vinyl acetate polymer, acrylic substituted cellulose acetate, non-degradable polyurethane, polystyrene, polyvinyl chloride, polyvinyl fluoride, poly(vinyl imidazole), chlorosulphonate polyolefins, polyethylene oxide, polyvinylpyrrolidone (PVP), polyethylene glycol (PEG), polymethacrylate, hydroxypropylmethylcellulose (HPMC), ethyl cellulose (EC), hydroxypropyl cellulose (HPC), cyclodextrin, copolymers of monomers forming these polymers, and cellulose.

More specifically, the biocompatible polymer may be a mixture of hyaluronic acid (HA) and gelatin.

Polymeric microparticles prepared using only hyaluronic acid are easily decomposed in vivo or under conditions such as acid and alkali, and therefore, their use is limited, cell adhesion is remarkably reduced, and the polymeric microparticles prepared by using only gelatin are significantly reduced in the mechanical properties.

In this regard, as a mixture of hyaluronic acid (HA) and gelatin is as a biocompatible polymer, excellent cell adhesion and mechanical properties can be realized at the same time.

Specifically, the first biocompatible polymer may include hyaluronic acid, and the second biocompatible polymer may include gelatin.

In the present disclosure, hyaluronic acid may include both hyaluronic acid itself and a hyaluronic acid salt. Therefore, the aqueous hyaluronic acid solution may be a concept that includes both an aqueous solution of hyaluronic acid, an aqueous solution of a hyaluronic acid salt, and a mixed aqueous solution of hyaluronic acid and a hyaluronic acid salt. The salt of hyaluronic acid salt may be inorganic salts such as sodium hyaluronate, potassium hyaluronate, calcium hyaluronate, magnesium hyaluronate, zinc hyaluronate, cobalt hyaluronate, organic salts such as hyaluronic acid tetrabutylammonium, and mixtures thereof.

In one embodiment of the present disclosure, the molecular weight of hyaluronic acid is not particularly limited, but is preferably 10,000 g/mol or more and 5,000,000 g/mol or less in order to realize various physical properties and biocompatibility.

As used herein, the gelatin may mean a protein obtained by treating collagen derived from an animal with acid or alkali and subsequently extracting it.

In one embodiment of the present disclosure, the molecular weight of gelatin is not particularly limited, but is preferably 10,000 g/mol or more and 5,000,000 g/mol or less in order to realize various physical properties and biocompatibility.

On the other hand, the polymeric microparticles may have a core-shell structure. As the polymer matrix included in the polymeric microparticles contains two or more types of biocompatible polymers, the core-shell structure can be implemented by a difference in reactivity between the biocompatible polymer and metal ion and an organic cros slinking agent containing at least one reactive functional group.

In the core-shell structure, the core may contain a polymer matrix in which hyaluronic acid is crosslinked through a metal ion and an organic crosslinking agent containing at least one reactive functional group, in an amount of more than 50% by volume, 60% by volume or more, 70% by volume or more, or 75% by volume or more with respect to the total volume of the polymer matrix contained in the core. Further, it may be contained in an amount of 100% by volume or less, less than 100% by volume, 95% by volume or less, or 90% by volume or less. Further, it may be contained in an amount of more than 50% by volume and less than 100% by volume, more than 50% by volume and less than 100% by volume, 60% by volume or more and less than 100% by volume, 60% by volume or more and 95% by volume or less, 70% by volume or more and 95% by volume or less, 70% by volume or more and 90% by volume or less, or 75% by volume or more and 90% by volume or less. That is, the core may include an excessive amount of hyaluronic acid with respect to gelatin.

Containing the polymer matrix in which hyaluronic acid is crosslinked through a metal ion and an organic crosslinking agent containing at least one reactive functional group in an amount of more than 50% by volume with respect to the total volume of the polymer matrix contained in the core can be seen by confirming visually or through a measurement equipment that the corresponding region is distributed in excess of 50% of the total region.

Specifically, the calculation of the ratio of the volume of the polymer matrix in which hyaluronic acid is crosslinked through a metal ion and an organic crosslinking agent containing at least one reactive functional group to the total volume of the polymer matrix included in the core is not particularly limited, and can be calculated by a normal measurement method. For example, it can be confirmed by taking an IR photograph of the hyaluronic acid characteristic peak (1080 $cm^{-1}$) relative to the gelatin characteristic peak (1650 $cm^{-1}$) of the prepared polymeric microparticles.

In the core-shell structure, the shell may contain a polymer matrix in which gelatin is crosslinked via a metal ion and an organic crosslinking agent containing at least one reactive functional group, in an amount of more than 50% by volume, 60% by volume or more, 70% by volume or more, or 75% by volume or more with respect to the total volume of the polymer matrix contained in the shell. Further, it may be contained in an amount of 100% by volume or less, less than 100% by volume, 95% by volume or less, or 90% by volume or less. Further, it may be contained in an amount of more than 50% by volume and less than 100% by volume, more than 50% by volume and less than 100% by volume, 60% by volume or more and less than 100% by volume, 60% by volume or more and 95% by volume or less, 70% by volume or more and 95% by volume or less, 70% by volume or more and 95% by volume or less, 70% by volume or more and 90% by volume or less, or 75% by volume or more and 90% by volume or less. That is, the shell may include an excessive amount of gelatin with respect to hyaluronic acid.

Containing the polymer matrix in which gelatin is crosslinked through a metal ion and an organic crosslinking agent containing at least one reactive functional group in an amount of more than 50% by volume with respect to the total volume of the polymer matrix contained in the core can be seen by confirming visually or through a measurement equipment that the corresponding region is distributed in excess of 50% of the total region.

The calculation of the ratio of the volume of the polymer matrix in which gelatin is crosslinked through a metal ion and an organic crosslinking agent containing at least one reactive functional group to the total volume of the polymer matrix included in the shell is not particularly limited, and can be calculated by a normal measurement method. For example, it can be confirmed by taking an IR photograph for the gelatin characteristic peak (1650 $cm^{-1}$) of the prepared polymeric microparticles.

A core-shell structure, which includes a core containing 50% by volume or more of a polymer matrix in which hyaluronic acid is crosslinked through a metal ion and an organic crosslinking agent containing at least one reactive functional group, and a shell containing 50% by volume or more of a polymer matrix in which gelatin is crosslinked through a metal ion and an organic crosslinking agent containing at least one reactive functional group, can be implemented depending on physicochemical factors such as solubility, temperature reactivity, and ionic bonding properties. More specifically, in the process for preparing polymeric microparticles, gelatin, which has low solubility in a polar solvent such as ethanol and has high temperature reactivity, can be reduced in fluidity and is fixed onto the particle surface to form a shell, whereby hyaluronic acid is relative more distributed inside the particle to form a core.

In particular, the method of preparing the polymeric microparticles of the embodiment includes the step of reacting a mixture containing a biocompatible polymer and a metal ion to form crosslinked polymer particles, before the step of further crosslinking the crosslinked polymer particles in a polar solvent phase including an organic crosslinking agent containing at least one reactive functional group, so that the core-shell structure may become clearer due to the ionic bond between the metal ion and the carboxyl group included in hyaluronic acid.

On the other hand, the polymeric microparticles may have the average diameter in distilled water of 1 μm or more, 1 μm or more and 450 μm or less, 100 μm or more and 450 μm or less, or 200 μm or more and 400 μm or less, or 300 μm or more and 400 μm or less. When the average diameter of the polymeric microparticles satisfies the above-mentioned range, cell adhesion and culture performance are excellent.

The average diameter may mean a diameter at 50 volume % point of cumulative distribution of particle numbers depending on the diameter.

In the polymeric microparticles of the one embodiment, the thickness of the shell may be 95% or less, 90% or less, 80% or less, 75% or less, 50% or less, 30% or less, 25% or less, or 20% or less of the longest diameter of the polymeric microparticles, based on the cross section having the longest diameter of the polymeric microparticles. Further, the thickness of the shell may be 0.01% or more, 1% or more, or 5% or more of the longest diameter of the polymeric microparticles, based on the cross section having the longest diameter of the polymeric microparticles.

In addition, the thickness of the core may be 5% or more, 10% or more, 20% or more, 25% or more, 50% or more, 70% or more, 75% or more, or 80% or more of the longest diameter of the polymeric microparticles, based on the cross section having the longest diameter of the polymeric microparticles of the one embodiment.

Further, the thickness of the core may be 99.99% or less, 99% or less, or 95% or less of the longest diameter of the polymeric microparticles, based on the cross section having the longest diameter of the polymeric microparticles.

Further, the polymeric microparticles may have a sphericity degree of 0.9 or more and 1.0 or less, 0.93 or more and 1.0 or less, 0.94 or more and 0.99 or less, or 0.94 or more and 0.98 or less.

The sphericity degree can be obtained by taking an optical photograph of the polymeric microparticles and calculating the average value of 30 to 100 arbitrary particles in the optical photograph.

Further, the polymeric microparticles may have an average compressive strength of 0.1 mN or more, 0.1 mN or more and 100 mN or less, 0.3 mN or more and 100 mN or less, 0.35 mN or more and 100 mN or less, 0.35 mN or more and 30 mN or less, 0.35 mN or more and 10 mN or less, or 0.35 mN or more and 3 mN or less, when deformed to a level of 25% of the average diameter with respect to the particles swollen with distilled water for 24 hours or more.

The average compressive strength may be a value in which a compressive strength when deformed to a level of 25% of the average diameter for n polymeric microparticles is divided by n.

For example, in the present disclosure, the average compressive strength may be a value in which a compressive strength when deformed to a level of 25% of the average diameter for 30 polymeric microparticles is divided by 30.

When the average compressive strength of the polymeric microparticles is less than 0.1 mN, a technical problem may occur in which the mechanical strength of the polymeric microparticles is deteriorated and the stability is reduced.

3. Medical Composition

According to another embodiment of the present disclosure, there can be provided a medical composition comprising the polymeric microparticles of the other embodiment and a pharmaceutically effective substance contained in the polymeric microparticles. The content concerning the polymeric microparticles may include all the content described above in the other embodiments.

The pharmaceutically active substance may exist in a state contained in the polymeric microparticles.

Examples of the pharmaceutically effective substance are not particularly limited, and an effective substance suitable for the application can be applied without limitation depending on the application of the polymeric microparticles of the one embodiment. That is, specific examples of the pharmaceutically effective substance are not limited, and examples thereof may include a drug selected from the group consisting of ampetaminil, arecolin, atrophine, bupranolol, buprenorphine, capsaicin, carisoprodol, chlorpromazine, ciclopirox olamine, cocaine, desipramine, dyclonine, epinephrine, ethosuximide, floxetine, hydromorphine, imipramine, lidocaine, methamphetamine, melproic acid, methylpenidate, morphine, oxibutynin, nadolol, nicotine, nitroglycerin, pindolol, prilocaine, procaine, propanolol, rivastigmine, scopolamine, selegiline, tulobuterol, valproic acid, Donepezil and the like, and a peptide or protein-based drug selected from the group consisting of EPO (Erythropoietin), human growth hormone (hGH), Exenatide, GLP-1 (glucagon-like peptide-1), insulin, CSF (granulocyte colony-stimulating factor), estrogen, progesterone, parathyroid hormone (PTH), and the like. All pharmacological substances in which pharmacological effects are proven are applicable without limitation.

The amount of the pharmaceutically effective substance added is also not particularly limited, and the content can be used without limitation depending on the application use and target. For example, the effective substance can be contained in an amount of 0.0001 parts by weight or more and 1000000 parts by weight or less with respect to 100 parts by weight of the polymeric microparticles. The effective substance may be contained in a small amount or an excessive amount without limitation with respect to the polymeric microparticles.

4. Cosmetic Composition

According to yet another embodiment of the present disclosure, there can be provided a cosmetic composition comprising the polymeric microparticles of the other embodiment and a cosmetically effective substance contained in the polymeric microparticles. The content concerning the polymeric microparticles may include all the content described above in the other embodiments.

The cosmetically active substance may exist in a state contained in the polymeric microparticles.

Examples of the cosmetically effective substance are not particularly limited, and an effective substance suitable for the application can be applied without limitation depending on the application of the polymeric microparticles of the one embodiment.

The amount of the pharmaceutically effective substance added is also not particularly limited, and the content can be used without limitation depending on the application use and target. For example, the effective substance can be included in an amount of 0.0001 parts by weight or more and 1000000 parts by weight or less with respect to 100 parts by weight of the polymeric microparticles. The effective substance may be contained in a small amount or an excessive amount without limitation with respect to the polymeric microparticles.

5. Medical Article

According to yet another embodiment of the present disclosure, there can be provided a medical article comprising the medical composition of the other embodiment. The content concerning the medical composition may include all the content described above in the other embodiments.

Examples of the medical article are not particularly limited, and in order to realize the characteristics of the present disclosure, it is suitable when used by inserting it into the body, or when strength must be maintained for a long period of time. For example, the medical article may include a body implant, an implantable drug delivery system, a transdermal patch, a wound treatment, and the like.

6. Cosmetic Article

According to a further embodiment of the present disclosure, there can be provided a cosmetic article comprising the cosmetic composition of the other embodiment. The content concerning the cosmetic composition may include all the content described above in the other embodiments.

Examples of the cosmetic article are not particularly limited, and in order to realize the characteristics of the present disclosure, for example, beauty creams, lotions, hair gels, packs (face masks) and the like can be mentioned.

Although the structure of the cosmetic pack is not particularly limited, it may include, for example, a support, and a cosmetically effective substance delivery layer formed on the support and including the polymeric microparticles of another embodiment. Examples of the support may include woven fabric, nonwoven fabric, silicone, polyethylene terephthalate, polyethylene, polypropylene, polyurethane, metal mesh, polyester, and the like.

Advantageous Effects

According to the present disclosure, a method of preparing polymeric microparticles that can realize excellent mechanical strength and cell adhesion, polymeric microparticles, medical compositions, cosmetic compositions, medical articles and cosmetic articles comprising the same can be provided.

Hereinafter, the present disclosure will be described in more detail by way of examples. However, these examples are for illustrative purposes only, and the scope of the present disclosure is not limited thereby.

EXAMPLE 1

Preparation of Polymeric Microparticles 200 mg of hyaluronic acid salt (weight average molecular weight: 500 kDa, maker: SK Bioland) was dissolved in 0.1N NaOH aqueous solution at 2 wt. %, and 250 mg of gelatin (gel strength: 300 g Bloom, maker: Sigma-Aldrich, product name G2500) was dissolved in distilled water at 2.5 wt. %. 10 mL of the respective solutions thus obtained were mixed to produce 20 mL of a mixed solution. To 80 mL of an ethanol solution added with 4 g of $FeCl_3$ as a compound containing iron ions ($Fe^{3+}$), the droplet of the mixed solution formed using an encapsulator (BUCHI, B-390) was added, subjected to a crosslinking reaction at 4° C. for 2 hours, and then washed with ethanol to prepare crosslinked particles.

2.2 g of 1,4-butandiol diglycidyl ether (BDDE) was mixed with 80% ethanol solution containing 20% 0.1N NaOH aqueous solution, to which the crosslinked particles were then added and subjected to a crosslinking reaction at room temperature for 3 days to prepare polymeric microparticles. The prepared particles were washed in the order of ethanol and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Figure 1:
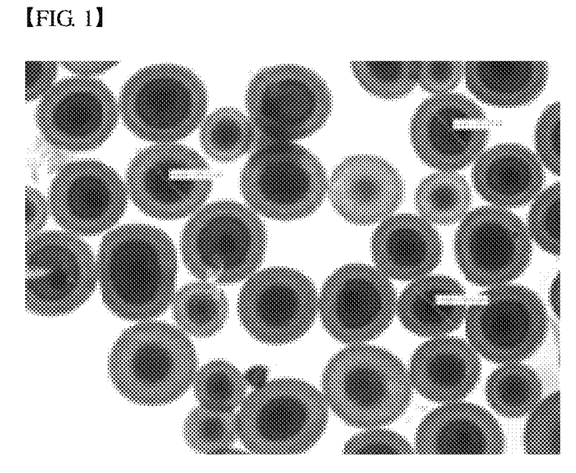
FIG. 1 is an optical microscope (OM) photograph of the polymeric microparticles of Example 1.

An optical microscope (OM) photograph of the prepared polymeric microparticles is shown in FIG. 1.

Figure 2:
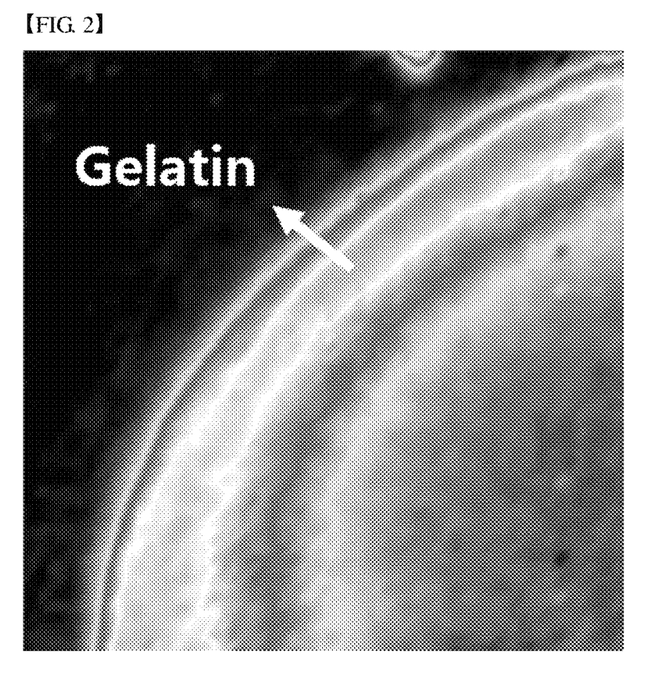
FIG. 2 is an IR photograph of the gelatin characteristic peak (1650 $cm^{-1}$) of the polymeric microparticles of Example 1.

An IR photograph of the gelatin characteristic peak (1650 $cm^{-1}$) of the prepared polymeric microparticles is shown in FIG. 2. It was confirmed that the portion containing gelatin was brightly displayed due to the difference in intensity of the characteristic peak (1650 $cm^{-1}$) of gelatin, and gelatin was distributed in the shell of the prepared polymeric microparticles.

Figure 3:
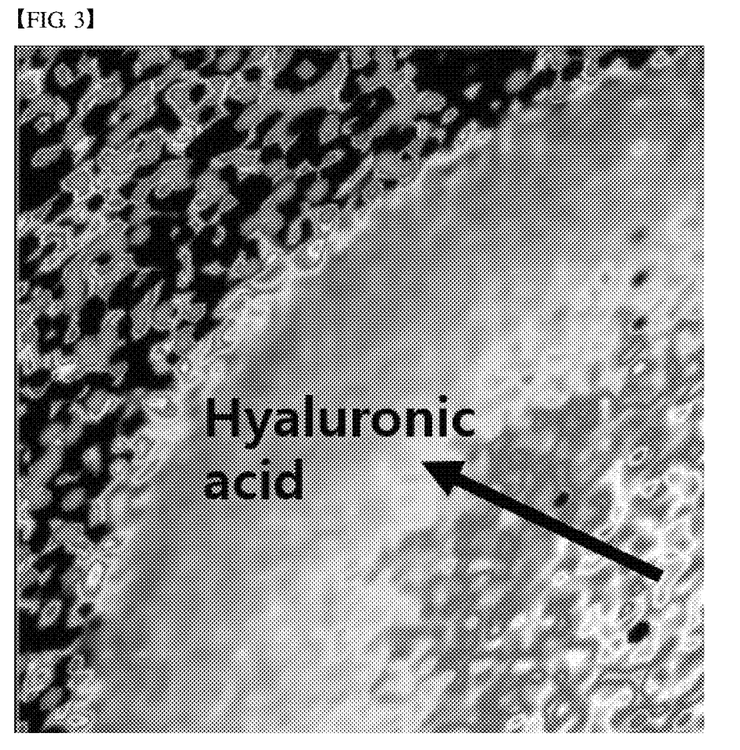
FIG. 3 is an IR photograph of the hyaluronic acid characteristic peak (1080 $cm^{-1}$) relative to the gelatin characteristic peak (1650 $cm^{-1}$) of the polymeric microparticles of Example 1.

An IR photograph of the hyaluronic acid characteristic peak (1080 $cm^{-1}$) relative to the gelatin characteristic peak (1650 $cm^{-1}$) of the prepared polymeric microparticles is shown in FIG. 3. It was confirmed that the portion containing hyaluronic acid in a high relative amount with respect to gelatin was displayed brightly, and hyaluronic acid was distributed in a relatively high amount compared to gelatin in the core of the prepared polymeric microparticles.

EXAMPLE 2

Preparation of Polymeric Microparticles

Polymeric microparticles were prepared in the same manner as in Example 1, except that an ethanol solution added with 4 g of $AlCl_3$ as a compound containing aluminum ions ($Al^{3+}$) was used instead of an ethanol solution added with 4 g of $FeCl_3$ as a compound containing iron ions ($Fe^{3+}$).

EXAMPLE 3

Preparation of Polymeric Microparticles

Polymeric microparticles were prepared in the same manner as in Example 1, except that 2.2 g of 50% glutaraldehyde was used instead of 2.2 g of 1,4-butandiol diglycidyl ether (BDDE).

Comparative Example 1

Preparation of Polymeric Microparticles

Hyaluronic acid salt (weight average molecular weight: 500 kDa, maker: SK Bioland) and gelatin (gel strength: 300 g Bloom, maker: Sigma-Aldrich, product name: G2500) were respectively dissolved in distilled water at 2 wt. % and 20 wt. % to prepare 5 ml each, and a mixed solution of these two solutions was mixed with a liquid paraffin solution to prepare a mixed solution containing a microemulsion. Then, 2.2 g of 1,4-butandiol diglycidyl ether (BDDE) as a crosslinking agent was added to the mixed solution, and subjected to a crosslinking reaction at room temperature for 5 days to prepare polymeric microparticles. The prepared particles were washed in the order of acetone, dichloromethane and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Comparative Example 2

Preparation of Polymeric Microparticles

Hyaluronic acid salt (weight average molecular weight: 500 kDa, maker: SK Bioland) was dissolved in 0.1N NaOH aqueous solution at 2 wt. %, and gelatin (gel strength: 300 g Bloom, maker: Sigma-Aldrich, product name G2500) was dissolved in distilled water at 2.5 wt. %. 10 mL of the respective solutions thus obtained were mixed to produce 20 mL. To 80 mL of an ethanol solution added with 4 g of $FeCl_3$ as a compound containing iron ions ($Fe^{3+}$), the droplet formed using an encapsulator (BUCHI, B-390) was added, subjected to a crosslinking reaction at 4° C. for 2 hours, and then washed with ethanol and distilled water to prepare crosslinked particles. The crosslinked particles were recovered using a sieve with a mesh size of 45 μm. The recovered crosslinked particles were filtered through a mesh sieve with a sieve size of 500 μm, and the remaining crosslinked particles were analyzed.

Comparative Example 3

Preparation of Polymeric Microparticles 200 mg of hyaluronic acid salt (weight average molecular weight: 500 kDa, maker: SK Bioland) was dissolved in 0.1 N NaOH aqueous solution at a concentration of 2 wt. %, and 250 mg of gelatin (gel strength: 300 g Bloom, maker: Sigma-Aldrich, product name G2500) was dissolved in distilled water at a concentration of 2.5 wt. % to produce 10 mL each. Then, a mixed solution of these two solutions was mixed with a liquid paraffin solution to prepare a mixed solution containing a microemulsion. Then, 2.2 g of 1,4-butandiol diglycidyl ether (BDDE) as a crosslinking agent was added to the mixed solution, and subjected to a crosslinking reaction at room temperature for 5 days. The prepared particles were washed in the order of acetone, dichloromethane, and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Comparative Example 4

Preparation of Polymeric Microparticles

Hyaluronic acid salt (weight average molecular weight: 500 kDa, maker: SK Bioland) was dissolved in 0.1 N NaOH aqueous solution at a concentration of 2 wt. %, and gelatin (gel strength: 300 g Bloom, maker: Sigma-Aldrich, product name G2500) was dissolved in distilled water at a concentration of 2.5 wt. % to prepare 5 ml each. Then, a mixed solution of these two solutions was mixed with a liquid paraffin solution to prepare a mixed solution containing a microemulsion. Then, 2.2 g of 1,4-butandiol diglycidyl ether (BDDE) as a crosslinking agent was added to the mixed solution, and subjected to a crosslinking reaction at room temperature for 5 days. The prepared particles were washed in the order of acetone, dichloromethane, and distilled water, and then the crosslinked particles were recovered using a sieve with a mesh size of 45 μm. The recovered crosslinked particles were filtered through a mesh sieve with a sieve size of 500 μm, and the remaining crosslinked particles were analyzed.

Comparative Example 5

Preparation of Polymeric Microparticles

Hyaluronic acid salt (weight average molecular weight: 500 kDa, maker: SK Bioland) and gelatin (gel strength: 300 g Bloom, maker: Sigma-Aldrich, product name: G2500) were respectively dissolved in distilled water at 2 wt. % and 2.5 wt. % to produce 5 mL each. Then, a mixed solution of these two solutions was mixed with a liquid paraffin solution to prepare a mixed solution containing a microemulsion. Then, to the mixed solution, 2.2 g of 1,4-butandiol diglycidyl ether (BDDE) as a crosslinking agent was added to the mixed solution, and subjected to a crosslinking reaction at room temperature for 5 days. The prepared particles were washed in the order of acetone, dichloromethane, and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Comparative Example 6

Preparation of Polymeric Microparticles

Alginate (maker: Sigma-Aldrich, product name: 180947) and cellulose (maker: Sigma-Aldrich, product name: C5678) were respectively dissolved in distilled water at 2.5 wt. %, and 10 mL of the respective solutions thus obtained were mixed to produce 20 mL. To 80 mL of an ethanol solution added with 4 g of $CaC_2$ as a compound containing calcium ion ($Ca^{2+}$), the droplet formed using an encapsulator (BUCHI, B-390) was added, subjected to a crosslinking reaction at room temperature for 2 hours, and then washed with ethanol to prepare crosslinked particles.

2.2 g of 1,4-butandiol diglycidyl ether (BDDE) was mixed with 80% ethanol solution containing 20% 0.1N NaOH aqueous solution, to which the crosslinked particles were then added and subjected to a crosslinking reaction at room temperature for 3 days to prepare polymeric microparticles. The prepared particles were washed in the order of ethanol and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Comparative Example 7

Preparation of Polymeric Microparticles 200 mg of hyaluronic acid salt (weight average molecular weight: 500 kDa, maker: SK Bioland) was dissolved in 0.1 N NaOH aqueous solution at a concentration of 2 wt. %, and 250 mg of gelatin (gel strength: 300 g Bloom, maker: Sigma-Aldrich, product name G2500) was dissolved in distilled water at a concentration of 2.5 wt. %. 10 mL of the respective solutions thus obtained were mixed to produce 20 mL. To 80 mL of an ethanol solution added with 4 g of $FeCl_3$ as a compound containing iron ion ($Fe^{3+}$), the droplet formed using an encapsulator (BUCHI, B-390) was added, and the mixture was subjected to a crosslinking reaction at 4° C. for 2 hours, and then washed with ethanol to prepare crosslinked particles.

The crosslinked particles were added to 80 mL of an ethanol solution added with 4 g of $CaCl_2$ as a compound containing calcium ion ($Ca^{2+}$), and subjected to a crosslinking reaction at 4° C. for 2 hours to prepare polymeric microparticles. The prepared particles were washed in the order of ethanol and distilled water, and then the crosslinked particles were recovered using a sieve with a mesh size of 45 μm. The recovered crosslinked particles were filtered through a sieve with a mesh size of 500 μm, and the remaining crosslinked particles were analyzed.

Experimental Example

Measurement of Physical Properties of Polymeric Microparticles

For the polymeric microparticles prepared in the above Examples and Comparative Examples, the average diameter, sphericity degree, strength, cell culture suitability, and stability of the polymeric microparticles were evaluated by the following methods.

1. Average Diameter

The average diameter of the polymeric microparticles of Examples and Comparative Examples in distilled water was measured using a laser particle size analyzer (Horiba, Partica LA-960).

2. Sphericity Degree

Optical (Olympus, BX53) photographs of the polymeric microparticles of Examples and Comparative Examples were taken, and the sphericity degree was calculated therefrom.

The sphericity degree according to the present disclosure was calculated as the average value of the ratio of the longest diameter to the shortest diameter (major axis/minor axis ratio) of 30 arbitrary particles in the optical photograph.

At this time, the closer the sphericity value 1 refers to the closer to the spherical shape.

3. Strength

For the polymeric microparticles of Examples and Comparative Examples, the strength of the microparticles was measured using a texture analyzer equipment. 30 microparticles swollen with distilled water for 24 hours were placed as a single layer on the region under the flat cylindrical probe of the equipment equipped with a 5 N load cell. The initial trigger force was set to 1 mN, and the particles were compressed at a rate of 1 mm/s. The force when deformed to a level of 25% of the average particle diameter was defined as the compressive force.

The average compressive strength was calculated by dividing the compressive force by 30, which is the number of microparticles to be measured.

4. Cell Culture Suitability

A cell culture medium was filled in a 6-well plate, polymeric microparticles and cells were added and the cells were cultured by plate-rock method. At this time, the temperature of the culture medium was maintained at 37° C., and the cells were cultured for 3 days, and the number of cells cultured with the polymeric microparticles was confirmed.

At this time, the cell culture suitability was evaluated based on the following criteria.

Suitable: when the number of cultured cells relative to the number of injected cells is 100% or more Unsuitable: when the number of cultured cells relative to the number of injected cells is less than 100%, or when microparticles are decomposed during culture 5. Stability The stability of the polymeric microparticles placed in phosphate-buffered saline solution during the sterilization process using a high-temperature and high-pressure sterilizer (Autoclave) and the particle stability after long-term culture were evaluated based on the following criteria:

Suitable: when the weight reduction rate of the dried polymeric microparticles before and after use of autoclave is 20% or less Unsuitable: when the weight reduction rate of the dried polymeric microparticles before and after use of autoclave exceeds 20%

TABLE 1

| Category | Average diameter (μm) | Sphericity degree | Average compressive strength (mN) | Cell culture suitability | Stability |
|---|---|---|---|---|---|
| Example 1 | 317 ± 21 | 0.95 ± 0.08 | 2.10 | Suitable | Suitable |
| Example 2 | 346 ± 26 | 0.96 ± 0.13 | 1.37 | Suitable | Suitable |
| Example 3 | 319 ± 32 | 0.95 ± 0.05 | 0.37 | Suitable | Suitable |
| Comparative Example 1 | 385 ± 13 | 0.98 ± 0.09 | 0.23 | Suitable | Unsuitable |
| Comparative Example 2 | 193 ± 21 | 0.96 ± 0.03 | 0.10 | Unsuitable | Unsuitable |
| Comparative Example 3 | Particle preparation impossible | | | | |
| Comparative Example 4 | Particle preparation impossible | | | | |
| Comparative Example 5 | Particle preparation impossible | | | | |
| Comparative Example 6 | 301 ± 48 | 0.94 ± 0.11 | 0.29 | Unsuitable | Suitable |
| Comparative Example 7 | 194 ± 17 | 0.95 ± 0.04 | 0.12 | Unsuitable | Unsuitable |

As shown in Table 1, it could be confirmed that in the polymeric microparticles of Examples, not only the number of cultured cells is 100% or more compared to the number of cells injected first, which is thus suitable for cell culture, but also the weight reduction rate of the dried polymeric microparticles before and after autoclave treatment appears to be 20% or less, which is thus suitable for sterilization treatment and long-term culture.

In addition, it could be confirmed that in the polymeric microparticles of Examples, the average compressive strength appears to be 0.37 mN or more, and thus excellent mechanical properties are realized and, at the same time, the proportion of particles exhibiting a high crosslinking density is high.

That is, the polymeric microparticles of Examples are suitable for cell culture, sterilization treatment, and long-term culture, and also can realize excellent crosslinking density and mechanical properties.

On the other hand, it could be confirmed that in the polymeric microparticles of Comparative Example 1, the weight reduction rate of the dried polymeric microparticles before and after autoclave treatment appears to be more than 20%, which is not suitable for sterilization and long-term culture, but also the average compressive strength appears to be 0.23 mN, indicating inferior mechanical properties, and the proportion of particles showing a low crosslinking density is high.

Moreover, it was observed that in the polymeric microparticles of Comparative Example 2, the polymer that was not crosslinked is dissolved in the distilled water washing step, so that the particles are contracted. Further, it could be confirmed that not only the microparticles are decomposed during cell culture, and the number of cultured cells compared to the number of injected cells is less than 100%, which is not suitable for cell culture, but also the weight reduction rate of the dried polymeric microparticles before and after autoclave treatment appears to be more than 20%, which is not suitable for sterilization treatment and long-term culture. Further, it could be confirmed that the average compressive strength appears to be 0.1 mN, showing inferior mechanical properties.

Further, it could be confirmed that in the polymeric microparticles of Comparative Examples 3 to 5, unlike Comparative Example 1, the concentration of the aqueous solution in which the biocompatible polymer was dissolved is adjusted to the same level as in Example 1, whereby the polymeric microparticles are not formed, and thus in the case of Examples, the polymeric microparticles can be formed even at a low biocompatible polymer concentration.

It could be confirmed that the polymeric microparticles of Comparative Example 6 exhibited an average compressive strength of 0.29 mN in distilled water state due to chemical crosslinking by the crosslinking agent, but they are not suitable for cell culture because alginate and cellulose, having no cell adhesion, are used as biocompatible polymers. In addition, by performing the crosslinking using calcium ions ($Ca^{2+}$) as a metal ion, it can react reversibly with the calcium ion present in the cell culture medium, and thus, the particle strength may be lowered during cell culture.

It could be confirmed that as the polymeric microparticles of Comparative Example 7 were prepared only through ionic crosslinking, some microparticles are degraded during sterilization and cell culture, which are not suitable for cell culture.

The invention claimed is:

1. A method of preparing polymeric microparticles comprising the steps of:
    subjecting a mixture containing a biocompatible polymer and a metal ion to a crosslinking reaction to form crosslinked polymer particles; and
    further crosslinking the crosslinked polymer particles in a polar solvent phase including an organic crosslinking agent containing at least one reactive functional group,
    wherein the biocompatible polymer comprises a mixture of hyaluronic acid and gelatin.

2. The method of claim 1, wherein:
    the step of subjecting a mixture containing a biocompatible polymer and a metal ion to a crosslinking reaction to form crosslinked polymer particles is performed in a polar solvent.

3. The method of claim 1, wherein:
    the step of subjecting a mixture containing a biocompatible polymer and a metal ion to a crosslinking reaction to form crosslinked polymer particles comprises
    forming an aqueous solution in which the biocompatible polymer is dissolved;

adding a compound containing the metal ion to a polar solvent to form a solution containing the metal ion; and mixing droplets of the aqueous solution in which the biocompatible polymer is dissolved and the solution containing the metal ion to form a mixed solution.

4. The method of claim 3, wherein:

the aqueous solution in which the biocompatible polymer is dissolved contains the biocompatible polymer in an amount of 0.01% by weight or more and 10% by weight or less with respect to the total weight of the aqueous solution in which the biocompatible polymer is dissolved.

5. The method of claim 3, wherein:

the compound containing the metal ion is contained in an amount of 200 parts by weight or more and 1000 parts by weight or less with respect to 100 parts by weight of the biocompatible polymer.

6. The method of claim 1, wherein:

in the step of further crosslinking the crosslinked polymer particles in a polar solvent phase including an organic crosslinking agent containing at least one reactive functional group, the organic crosslinking agent containing at least one reactive functional group is contained in an amount of 150 parts by weight or more and 1000 parts by weight or less with respect to 100 parts by weight of the biocompatible polymer.

7. The method of claim 1, wherein:

the organic crosslinking agent containing at least one reactive functional group comprises at least one formyl group or epoxy group.

8. The method of claim 1, wherein:

the mixture of hyaluronic acid and gelatin contains the gelatin in an amount of 50 parts by weight or more and 500 parts by weight or less with respect to 100 parts by weight of the hyaluronic acid.

9. Polymeric microparticles having a core-shell structure, comprising:

a core including a first biocompatible polymer, a metal ion, and an organic crosslinking agent containing at least one reactive functional group; and a shell surrounding all or part of the core and including a second biocompatible polymer, a metal ion, and an organic crosslinking agent containing at least one reactive functional group, wherein the first biocompatible polymer comprises hyaluronic acid, and the second biocompatible polymer comprises gelatin.

10. The polymeric microparticles of claim 9, wherein:

the core comprises a polymer matrix in which the first biocompatible polymer is crosslinked through the metal ion and the organic crosslinking agent containing at least one reactive functional group, and the shell comprises a polymer matrix in which the second biocompatible polymer is crosslinked through the metal ion and the organic crosslinking agent containing at least one reactive functional group.

11. The polymeric microparticles of claim 10, wherein:

the core contains a polymer matrix in which hyaluronic acid is crosslinked through the metal ion and the organic crosslinking agent containing at least one reactive functional group, in an amount of more than 50% by volume of with respect to the total volume of the polymer matrix contained in the core.

12. The polymeric microparticles of claim 10, wherein:

the shell contains a polymer matrix in which gelatin is crosslinked through the metal ion and the organic crosslinking agent containing at least one reactive functional group, in an amount of more than 50% by volume with respect to the total volume of the polymer matrix contained in the shell.

13. The polymeric microparticles of claim 9, wherein:

a thickness of the shell is 95% or less of a longest diameter of the polymeric microparticles, based on a cross section having the longest diameter of the polymeric microparticles.

14. The polymeric microparticles of claim 9, wherein:

the organic crosslinking agent containing at least one reactive functional group comprises a crosslinking agent having 1 to 30 carbon atoms and containing at least one reactive functional group.

15. A medical composition comprising the polymeric microparticles of claim 9 and a pharmaceutically effective substance contained in the polymeric microparticles.

16. A medical article comprising the medical composition of claim 15.

17. A cosmetic composition comprising the polymeric microparticles of claim 9 and a cosmetically effective substance contained in the polymeric microparticles.

18. A cosmetic article comprising the cosmetic composition of claim 17.

* * * * *